United States Patent
Yasui et al.

(10) Patent No.: US 11,692,993 B2
(45) Date of Patent: Jul. 4, 2023

(54) TISSUE PAPER AND METHOD OF EVALUATING THE SAME

(71) Applicants: DAIO PAPER CORPORATION, Shikokuchuo (JP); TOHOKU UNIVERSITY, Sendai (JP)

(72) Inventors: Shuta Yasui, Fujinomiya (JP); Hidenori Yorozu, Tokyo (JP); Kazuo Hokkirigawa, Sendai (JP); Takeshi Yamaguchi, Sendai (JP); Kei Shibata, Sendai (JP); Naoya Yamai, Sendai (JP); Risa Nakane, Sendai (JP)

(73) Assignees: DAIO PAPER CORPORATION, Ehime (JP); TOHOKU UNIVERSITY, Miyagi (JP)

( * ) Notice: Subject to any disclaimer, the term of this patent is extended or adjusted under 35 U.S.C. 154(b) by 268 days.

(21) Appl. No.: 16/762,896

(22) PCT Filed: Oct. 29, 2018

(86) PCT No.: PCT/JP2018/040109
§ 371 (c)(1),
(2) Date: May 8, 2020

(87) PCT Pub. No.: WO2019/093179
PCT Pub. Date: May 16, 2019

(65) Prior Publication Data
US 2021/0172925 A1 Jun. 10, 2021

(30) Foreign Application Priority Data
Nov. 9, 2017 (JP) ................. 2017-216725

(51) Int. Cl.
*G01N 33/34* (2006.01)
*A47K 10/16* (2006.01)
*D21H 27/00* (2006.01)

(52) U.S. Cl.
CPC ............. *G01N 33/34* (2013.01); *A47K 10/16* (2013.01)

(58) Field of Classification Search
CPC ...... G01N 33/34; A47K 10/16; D21H 27/002; D21H 27/004; D21H 27/005; D21H 27/30; D21H 25/00; B32B 5/00
See application file for complete search history.

(56) References Cited

U.S. PATENT DOCUMENTS

| 6,740,609 B1 | 5/2004 | Peng et al. |
| 9,157,185 B2 * | 10/2015 | Inoue ...................... D21F 3/029 |

(Continued)

FOREIGN PATENT DOCUMENTS

| CN | 1338532 A | 3/2002 |
| JP | 1998-226986 A | 8/1998 |

(Continued)

OTHER PUBLICATIONS

English Translation of WO-2016204078-A1 (Year: 2016).*
English Translation of JP-2004187930-A (Year: 2004).*

*Primary Examiner* — Maria V Ewald
*Assistant Examiner* — Daniel P Dillon
(74) *Attorney, Agent, or Firm* — Arthur M. Reginelli; Renner, Kenner

(57) ABSTRACT

To provide tissue paper excellent in softness and smoothness. In tissue paper that is two-ply non-moisturizing tissue paper to which no chemical solution is applied, a basis weight per sheet is 10.0 to 18.0 g/m², the thickness of two plies is 100 to 240 μm, a dry tensile strength in the paper horizontal direction is 70 to 180 cN/25 mm, a wet tensile strength in the paper horizontal direction is 25 to 55 cN/25 mm, and a free sensory evaluation value $E_f$ calculated (Continued)

according to the following Equation 1 is 3.7 to 6.6, and a slip sensory evaluation value $E_s$ calculated according to the following Equation 2 is 5.0 to 8.2.

Free sensory evaluation value $E_f$=−2.879×(dry tensile strength in paper horizontal direction)+6.55×(wet tensile strength in paper horizontal direction)+5.36  (Equation 1)

Slip sensory evaluation value $E_s$=−8.80×(dynamic friction coefficient)−0.41×(arithmetic mean surface roughness)+13.58  (Equation 2)

1 Claim, 7 Drawing Sheets

(56) References Cited

U.S. PATENT DOCUMENTS

| 2004/0112783 | A1 | 6/2004 | Mukai et al. |
| 2008/0258592 | A1 | 10/2008 | Blum |
| 2014/0076511 | A1 | 3/2014 | Inoue et al. |

FOREIGN PATENT DOCUMENTS

| JP | 2003-024282 A | | 1/2003 | |
| JP | 2004-187930 A | | 4/2004 | |
| JP | 2004187930 A | * | 7/2004 | |
| JP | 2008-064722 A | | 3/2008 | |
| JP | 2017-05508 A | | 3/2017 | |
| JP | 2017-055807 A | | 3/2017 | |
| WO | 2008/050244 A2 | | 5/2008 | |
| WO | 2016/204078 A1 | | 12/2016 | |
| WO | WO-2016204078 A1 | * | 12/2016 | ............. A47K 10/16 |

* cited by examiner

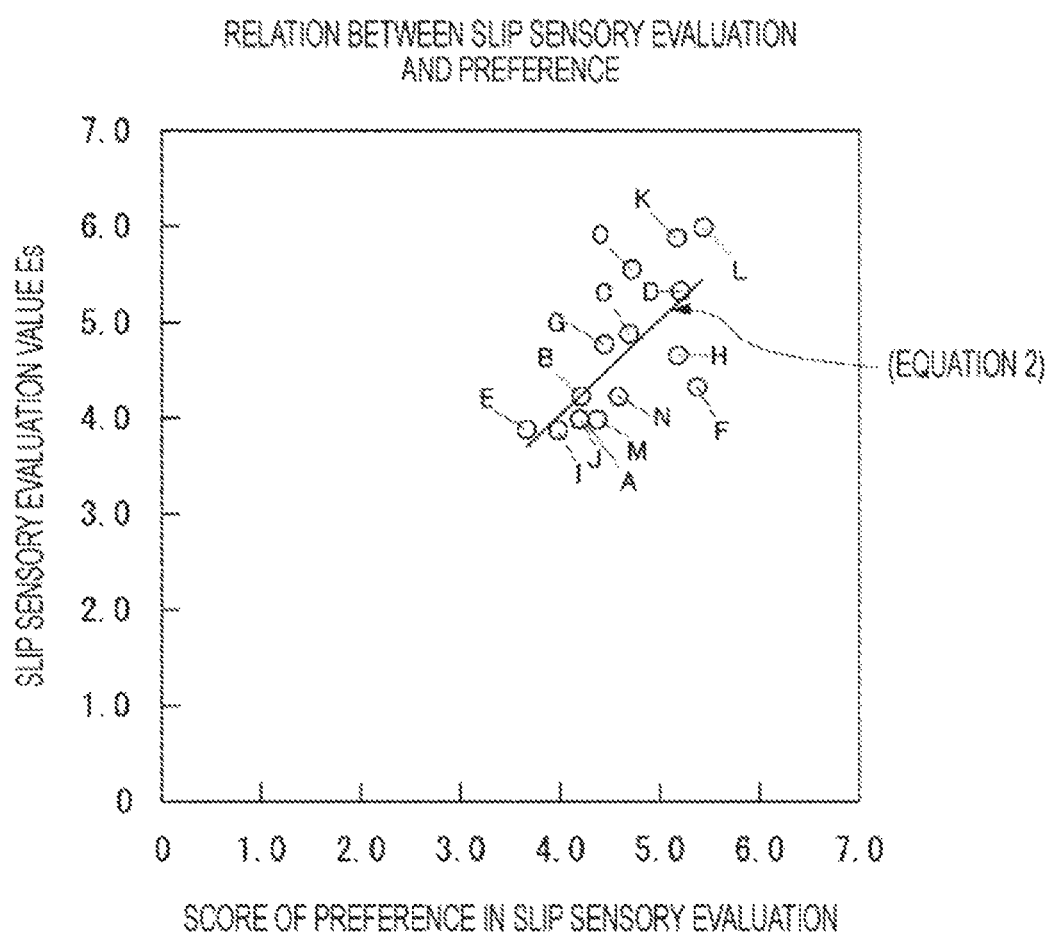

TISSUE PAPER AND METHOD OF EVALUATING THE SAME

TECHNICAL FIELD

The present invention relates to tissue paper and a method of evaluating tissue paper.

BACKGROUND ART

The usability of tissue paper is generally evaluated by a sensory evaluation in which each evaluation item such as "softness", "smoothness", "durability", and "bulkiness" is set, and a plurality of subjects judges the usability by comparing with reference samples for each item, and numerically evaluates each item.

On the other hand, the characteristics of tissue paper are determined by dry tensile strength when dry or wet, elongation at break, basis weight, paper thickness, moisture content, and softness (bending resistance), MMD, friction coefficient, surface roughness, and other paper quality parameters.

However, the relationship between the paper quality parameter of tissue paper and the sensory evaluation value is often unclear, and it has been difficult to quantitatively evaluate the usability of tissue paper. In addition, in the conventional sensory evaluation, the difference in the criteria of each item for each subject is not examined in detail. In particular, for "softness" and "smoothness", the sense that a subject feels "soft" may include many cases where another subject feels "smooth". Therefore, if those are determined as respective items, accuracy may be reduced.

For this reason, in the design and development of tissue paper, the adjustment of raw materials and the adjustment of a production method are repeatedly performed such that the physical properties that may affect the sensory evaluation for each item such as "softness", "smoothness", "durability", and "bulkiness" described above are changed. However, tissue paper is a very thin crepe paper and often requires preparation of samples in large-scale production facilities. Therefore, speeding up the development is difficult and the cost is increased.

As described above, the conventional evaluation method of tissue paper based on sensory evaluation has points to be improved in terms of accuracy, development speed, cost, and the like, and also, in designing and developing tissue paper, a new method for evaluating the usability of tissue paper is required. In particular, when consumers evaluate tissue paper as a product, importance is placed on price, softness, and good texture.

CITATION LIST

Patent Literature

Patent Literature 1: JP 2017-55807A
Patent Literature 2: JP H10-226986A
Patent Literature 3: JP 2003-24282A
Patent Literature 4: JP 2008-64722A

SUMMARY OF INVENTION

Technical Problem

Therefore, a main object of the present invention is to provide tissue paper having excellent softness and smoothness, and a method of evaluating tissue paper by evaluating the softness and smoothness thereof.

Solution to Problem

Means for solving the above problems are as follows.

First Means

In tissue paper that is two-ply non-moisturizing tissue paper to which no chemical solution is applied,
a basis weight per sheet is 10.0 to 18.0 g/m², the thickness of two plies is 100 to 240 μm,
a dry tensile strength in the paper horizontal direction is 70 to 180 cN/25 mm,
a wet tensile strength in the paper horizontal direction is 25 to 55 cN/25 mm, and
a free sensory evaluation value $E_f$ calculated according to the following Equation 1 is 3.7 to 6.6, and a slip sensory evaluation value $E_s$ calculated according to the following Equation 2 is 5.0 to 8.2.

Free sensory evaluation value $E_f$=−2.879×(dry tensile strength in paper horizontal direction)+6.55×(wet tensile strength in paper horizontal direction)+5.36    (Equation 1)

Slip sensory evaluation value $E_s$=−8.80×(dynamic friction coefficient)−0.41×(arithmetic mean surface roughness)+13.58    (Equation 2)

Second Means

In tissue paper that is a two-ply moisturizing tissue paper to which a chemical solution is applied,
a basis weight per sheet is 14.0 to 22.0 g/m², a thickness is 120 to 250 μm,
a dry tensile strength in the paper horizontal direction is 50 to 120 cN/25 mm,
a wet tensile strength in the paper horizontal direction is 30 to 90 cN/25 mm,
the free sensory evaluation value $E_f$ calculated according to the following Equation 1 is 6.0 to 8.4, and the slip sensory evaluation value $E_s$ calculated according to Equation 2 is 5.3 to 8.0.

Free sensory evaluation value $E_f$=−2.879×(dry tensile strength in paper horizontal direction)+6.55×(wet tensile strength in paper horizontal direction)+5.36    (Equation 1)

Slip sensory evaluation value $E_s$=−8.80×(dynamic friction coefficient)−0.41×(arithmetic mean surface roughness)+13.58    (Equation 2)

Third Means

A method of evaluating tissue paper, includes
a free sensory evaluation step of scoring a plurality of sheets of tissue paper with different physical property values by freely touching the tissue paper and scoring the tissue paper based on a criteria of "like" or "dislike",
a slip sensory evaluation step of scoring a plurality of sheets of tissue paper having different physical property values by scoring a feeling of slipping when tissue paper fixed on a horizontal table is slipped with a finger, based on the criteria of "like" or "dislike",
a free sensory evaluation analysis step of performing a multiple regression analysis by a stepwise method using results of the free sensory evaluation as objective variables and paper quality parameters of tissue paper as explanatory variables,
a slip sensory evaluation analysis step of performing a multiple regression analysis by a stepwise method using results of the slip sensory evaluation as objective variables and paper quality parameters of tissue paper as explanatory variables, and an evaluation step of evaluating tissue paper from a free sensory evaluation value calculated according to a regression equation obtained in the free sensory evaluation analysis step, and a slip sensory evaluation value calculated according to a regression equation obtained in the slip sensory evaluation analysis step.

Advantageous Effects of Invention

According to the present invention described above, there are provided tissue paper having excellent softness and smoothness, and a method of evaluating the tissue paper by evaluating the softness and smoothness thereof.

BRIEF DESCRIPTION OF DRAWINGS

FIG. 7 is a graph for explaining a correlation equation (Equation 2) according to the present invention.

DESCRIPTION OF EMBODIMENTS

Figure 1:
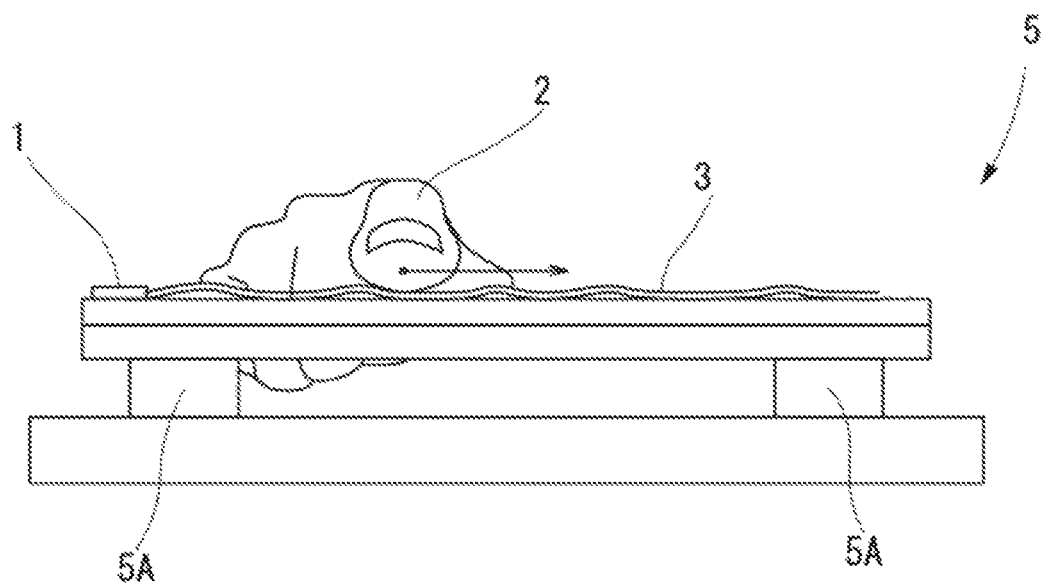
FIG. 1 is a view for explaining a measurement method of a dynamic friction coefficient according to the present invention.

Hereinafter, embodiments of the present invention will be described.

[Method of Evaluating Tissue Paper]

A method of evaluating tissue paper according to the present invention will be described.

A method of evaluating tissue paper according to the present invention mainly includes five steps: (1) free sensory evaluation step of scoring a plurality of sheets of tissue paper with different physical property values by freely touching the tissue paper and scoring the tissue paper based on the criteria of "like" or "dislike", (2) slip sensory evaluation step of scoring a plurality of sheets of tissue paper having different physical property values by scoring the feeling of slipping when tissue paper fixed on a horizontal table is slipped with a finger, based on the criteria of "like" or "dislike", (3) free sensory evaluation analysis step of performing a multiple regression analysis by a stepwise method using results of the free sensory evaluation as objective variables and paper quality parameters of tissue paper as explanatory variables, (4) slip sensory evaluation analysis step of performing a multiple regression analysis by a stepwise method using results of the slip sensory evaluation as objective variables and paper quality parameters of tissue paper as explanatory variables, and (5) evaluation step of evaluating tissue paper from a free sensory evaluation value calculated according to a regression equation obtained in the free sensory evaluation analysis step, and a slip sensory evaluation value calculated according to a regression equation obtained in the slip sensory evaluation analysis step. Note that, either of the free sensory evaluation step (1) and the slip sensory evaluation step (2) may be performed first. Further, the free sensory evaluation step (1) and the free sensory evaluation analysis step (3) may be performed in series. Similarly, the slip sensory evaluation step (2) and the slip sensory evaluation step (4) may be performed in series.

In the free sensory evaluation step, instead of performing a sensory evaluation on each item such as "softness", "smoothness", "durability", and "bulkiness" as in the conventional evaluation, and evaluating each item, a free sensory evaluation is performed in which tissue paper is scored based on the criteria of "like" or "dislike" by freely touching the tissue paper. Note that it is desirable that the number of evaluators be nine or more. In addition, it is desirable that one evaluator evaluate the same sample (although a notation is changed) five times, an abnormal value be omitted, and the average value of evaluation points be used as the evaluation value of the evaluator. The scoring in the free sensory evaluation may be performed by setting the score of most commonly used sample on the market (sample A in the table) to four points, scoring each sample with one to seven points, and calculating the average value of each evaluator.

As described in the background art, in the case of performing sensory evaluation on multiple conventional items, particularly with tissue paper, "softness" felt by a subject may be felt by other subjects as "smoothness". Given that there is a gap in the sense of criteria between the subjects, if "softness" and "smoothness" are evaluated differently, this is one of the factors that reduce the accuracy and reliability of the evaluation results. Since the free sensory evaluation performed in the free sensory evaluation step according to the present invention is first evaluated by one item, there is no room for sensory deviation between subjects for each item. This free sensory evaluation according to the present invention is not performed for each specific item such as conventional "softness", and it is characterized in that the tissue paper is freely touched and scored based on the criteria of "like" or "dislike". On the other hand, the result of the free sensory evaluation is mainly similar to how the subject feels as "softness". It has been confirmed as follows that this free sensory evaluation is similar to the feeling mainly felt as "softness".

Figure 2:
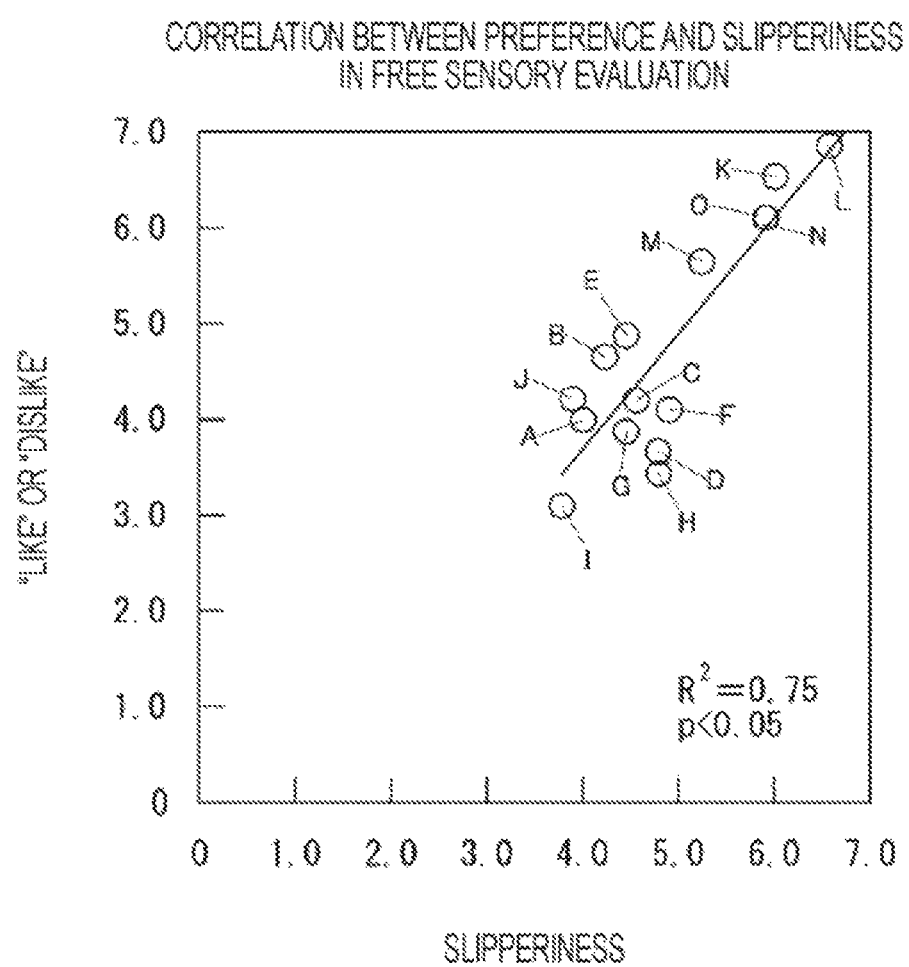
FIG. 2 is a graph indicating results of "preference" and "slipperiness" in a free sensory evaluation.
Figure 3:
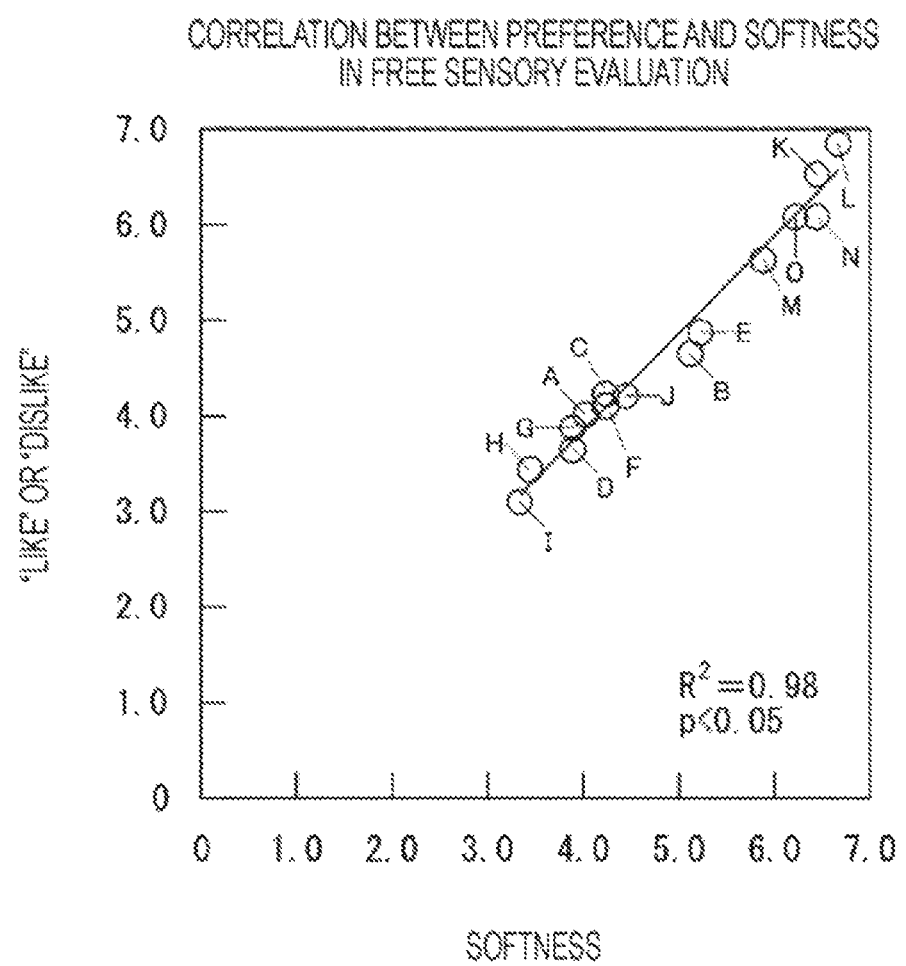
FIG. 3 is a graph indicating results of "preference" and "softness" in a free sensory evaluation.

As illustrated in Table 1 below, commercially available five types of moisturizing tissue paper, three types of luxury non-moisturizing tissue paper products, and seven types of general-purpose non-moisturizing tissue paper products are scored according to the criteria of "like" or "dislike" by freely touching tissue paper, and at the same time, also scored for "softness" and "slipperiness". Regarding the relationship between "slipperiness" and "softness" to the judgment of "like" or "dislike", the results are as indicated in FIGS. 2 and 3, and in order to explain the judgment of "like" or "dislike" in the free sensory evaluation, "softness" is more applicable than "slipperiness". Note that the tissue paper generally has a product category of moisturizing tissue paper, luxury non-moisturizing tissue paper products, and general-purpose non-moisturizing tissue paper products.

On the other hand, in the slip sensory evaluation step, multiple sheets of tissue paper with different physical property values are scored by the slip sensory evaluation in which the feeling of slipping when sliding with the finger on tissue paper fixed on a horizontal table is scored based on the criteria of "like" or "dislike". Note that it is desirable that the number of evaluators be nine or more. In addition, it is desirable that one evaluator evaluate the same sample (although a notation is changed) five times, an abnormal value be omitted, and the average value of evaluation points be used as the evaluation value of the evaluator. The scoring in the free sensory evaluation may be performed by setting the score of most commonly used sample on the market (sample A in the table) to four points, scoring each sample with one to seven points, and calculating the average value of each evaluator.

Figure 4:
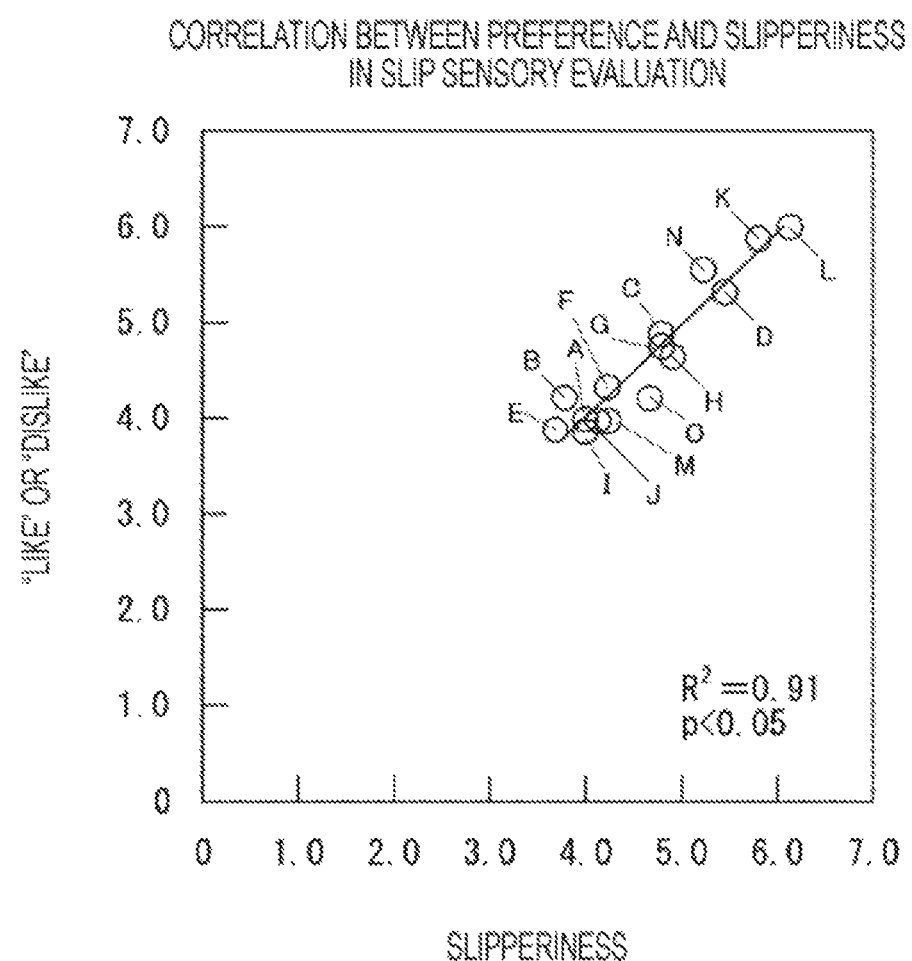
FIG. 4 is a graph indicating results of "preference" and "slipperiness" in a slip sensory evaluation.
Figure 5:
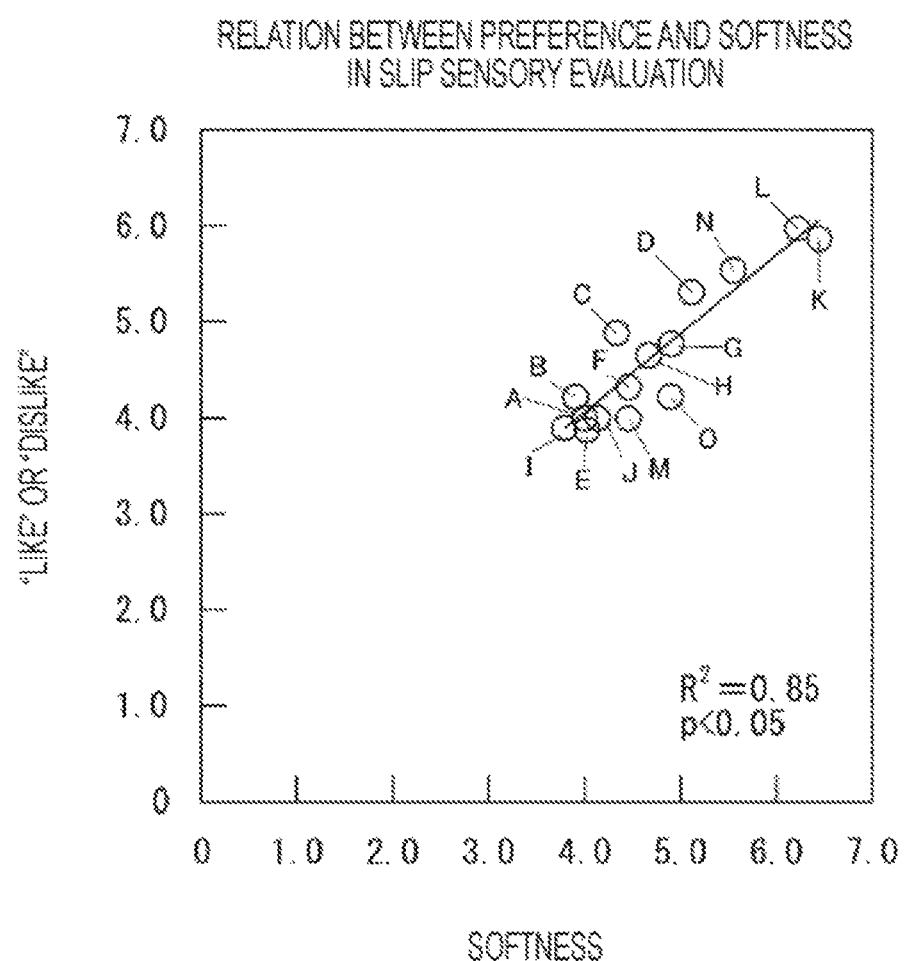
FIG. 5 is a graph indicating results of "preference" and "softness" in a slip sensory evaluation.

In this slip sensory evaluation, an operation of sliding with the finger on tissue paper fixed on a horizontal table is performed. Therefore, feeling about bending of reference tissue paper is eliminated, and the subject's feeling of "softness" is considerably eliminated, and substantially "slipperiness" can be evaluated. In addition, while the operation of the slip sensory evaluation step according to the present invention is particularly limited to sliding, the evaluation is performed by scoring according to the criteria of "like" or "dislike" in the evaluation criteria. For that reason, evaluation is performed from the viewpoint of the texture of tissue paper without simply determining whether the tissue paper is slippery. It has been confirmed in the same manner as the free sensory evaluation that the result of the slip sensory evaluation is mainly similar to how the subject feels as "slipperiness". That is, as illustrated in Table 1 below, for commercially available five types of moisturizing tissue paper, five types of luxury non-moisturizing tissue paper products, and five types of general-purpose non-moisturizing tissue paper products, the feeling of slipping when sliding with a finger on tissue paper fixed on a horizontal table is scored according to the criteria of "like" or "dislike" and at the same time, also scored for "softness" and "slipperiness". Regarding the relationship between "slipperiness" and "softness" to the judgment of "like" or "dislike" in the slip sensory evaluation, the results are as indicated in FIGS. 4 and 5, and in order to explain the judgment of "like" or "dislike" in the slip sensory evaluation, "slipperiness" is more applicable than "softness".

In the free sensory evaluation analysis step, a multiple regression analysis by a stepwise method is performed using the result of the free sensory evaluation in the free sensory evaluation step as an objective variable and the paper quality parameter of tissue paper as an explanatory variable. Specifically, the characteristics of tissue paper are generally characterized by the dry tensile strength when dry or wet, elongation at break, basis weight, paper thickness, moisture content, and paper quality parameters such as softness (bending resistance), MMD, dynamic friction coefficient, and surface roughness. Therefore, multiple regression analysis is performed with the objective variable as the result of the free sensory evaluation and the explanatory variable as the dry tensile strength when dry or wet, elongation at break, basis weight, paper thickness, moisture content, softness (bending resistance), MMD, friction coefficient, and surface roughness. The multiple regression analysis is again performed after finding the one with high correlation coefficient between objective variable and each explanatory variable, and in the case where there is the one with higher correlation coefficient between two explanatory variables, excluding the one explanatory variable therefrom. By repeating this, the explanatory variables are narrowed down, and the evaluation equation is determined.

TABLE 1

| | | | MOISTURIZING COMMERCIAL PRODUCT K | MOISTURIZING COMMERCIAL PRODUCT L | MOISTURIZING COMMERCIAL PRODUCT M | MOISTURIZING COMMERCIAL PRODUCT N | MOISTURIZING COMMERCIAL PRODUCT O |
|---|---|---|---|---|---|---|---|
| CHEMICAL SOLUTION APPLICATION | CHEMICAL SOLUTION APPLICATION | APPLIED/ NOT APPLIED | APPLIED | APPLIED | APPLIED | APPLIED | APPLIED |
| | APPLICATION METHOD | ONE SURFACE/ BOTH SURFACES | BOTH SURFACES | BOTH SURFACES | ONE SURFACE | BOTH SURFACES | BOTH SURFACES |
| | LOTION CHEMICAL SOLUTION APPLICATION AMOUNT | % BY MASS | 25.5 | 24.3 | 15.0 | 20.0 | 19.5 |
| PAPER QUALITY PARAMETER | BASIS WEIGHT (1 SHEET) | $g/m^2$ | 17.5 | 18.0 | 14.7 | 16.2 | 14.3 |
| | NUMBER OF PLIES | SHEETS | 2 | 2 | 2 | 2 | 2 |
| | PAPER THICKNESS | μm | 145 | 174 | 123 | 166 | 139 |
| | DRY STRENGTH IN LONGITUDINAL DIRECTION | cN/25 mm | 194.0 | 238.0 | 253.0 | 330.0 | 216.0 |
| | DRY STRENGTH IN HORIZONTAL DIRECTION | cN/25 mm | 80.0 | 51.0 | 73.0 | 85.0 | 83.0 |

TABLE 1-continued

|  |  |  |  |  |  |  |  |
|---|---|---|---|---|---|---|---|
|  | ELONGATION (LONGITUDINAL DIRECTION) | % | 12.4 | 14.5 | 13.1 | 11.3 | 14.6 |
|  | WET STRENGTH IN HORIZONTAL DIRECTION | cN/25 mm | 50.0 | 32.0 | 34.0 | 41.0 | 51.0 |
|  | SURFACE ROUGHNESS | μm | 10.0 | 8.5 | 9.7 | 8.6 | 9.7 |
|  | AVERAGE FRICTION COEFFICIENT | — | 0.48 | 0.47 | 0.52 | 0.54 | 0.50 |
|  | SOFTNESS | cN/100 mm | 0.9 | 1.0 | 0.7 | 0.8 | 0.9 |
|  | MMD | — | 8.2 | 5.6 | 7.7 | 6.4 | 7.4 |
|  | WEB VOLUME | mm | 80.0 | 83.0 | 58.0 | 82.0 | 60.0 |
|  | MOISTURE PERCENTAGE | % | 12.6 | 8.6 | 9.0 | 9.3 | 10.3 |
| EVALUATION EQUATION | (EQUATION 1) FREE SENSORY EVALUATION VALUE Ef = −2.879 × (DRY TENSILE STRENGTH IN PAPER HORIZONTAL DIRECTION) + 6.55 × (WET TENSILE STRENGTH IN PAPER HORIZONTAL DIRECTION) + 5.36 |  | 6.3 | 6.0 | 5.5 | 5.6 | 6.3 |
|  | (EQUATION 2) SLIP SENSORY EVALUATION VALUE Es = −8.80 × (DYNAMIC FRICTION COEFFICIENT) − 0.41 × (ARITHMETIC MEAN SURFACE ROUGHNESS) + 13.58 |  | 5.3 | 6.0 | 5.0 | 5.3 | 5.2 |
| SENSORY EVALUATION RESULT | EVALUATION OF "PREFERENCE" |  | 5.9 | 6.0 | 4.0 | 5.6 | 4.2 |
|  | EVALUATION OF PREFERENCE OF "SOFTNESS" |  | 6.5 | 6.9 | 5.7 | 6.1 | 6.1 |
|  | EVALUATION OF PREFERENCE OF "SLIPPERINESS" |  | 5.9 | 6.0 | 4.0 | 5.6 | 4.2 |

|  |  |  | NON-MOISTURIZING (GENERAL-PURPOSE PRODUCT) COMMERCIAL PRODUCT A | NON-MOISTURIZING (LUXURY PRODUCT) COMMERCIAL PRODUCT B | NON-MOISTURIZING (GENERAL-PURPOSE PRODUCT) COMMERCIAL PRODUCT C | NON-MOISTURIZING (GENERAL-PURPOSE PRODUCT) COMMERCIAL PRODUCT D | NON-MOISTURIZING (LUXURY PRODUCT) COMMERCIAL PRODUCT E |
|---|---|---|---|---|---|---|---|
| CHEMICAL SOLUTION APPLICATION | CHEMICAL SOLUTION APPLICATION | APPLIED/ NOT APPLIED | NOT APPLIED | NOT APPLIED | NOT APPLIED | NOT APPLIED | NOT APPLIED |
|  | APPLICATION METHOD | ONE SURFACE/ BOTH SURFACES | — | — | — | — | — |
|  | LOTION CHEMICAL SOLUTION APPLICATION AMOUNT | % BY MASS | 0 | 0 | 0 | 0 | 0 |
| PAPER QUALITY PARAMETER | BASIS WEIGHT (1 SHEET) | g/m² | 13.3 | 16.1 | 13.3 | 11.0 | 14.6 |
|  | NUMBER OF PLIES | SHEETS | 2 | 2 | 2 | 2 | 2 |
|  | PAPER THICKNESS | μm | 142 | 190 | 123 | 101 | 205 |

TABLE 1-continued

| | | | | | | | |
|---|---|---|---|---|---|---|---|---|
| | DRY STRENGTH IN LONGITUDINAL DIRECTION | cN/25 mm | 394.0 | 289.3 | 259.0 | 524.0 | 320.5 |
| | DRY STRENGTH IN HORIZONTAL DIRECTION | cN/25 mm | 90.0 | 102.0 | 142.0 | 161.0 | 84.0 |
| | ELONGATION (LONGITUDINAL DIRECTION) | % | 14.3 | 14.2 | 13.5 | 14.8 | 14.0 |
| | WET STRENGTH IN HORIZONTAL DIRECTION | cN/25 mm | 30.0 | 35.0 | 36.0 | 37.0 | 30.0 |
| | SURFACE ROUGHNESS | μm | 10.5 | 8.6 | 10.0 | 8.1 | 10.4 |
| | AVERAGE FRICTION COEFFICIENT | — | 0.50 | 0.60 | 0.47 | 0.51 | 0.56 |
| | SOFTNESS | cN/100 mm | 1.1 | 1.1 | 1.2 | 1.0 | 0.9 |
| | MMD | — | 7.0 | 5.7 | 7.8 | 7.0 | 7.4 |
| | WEB VOLUME | mm | 62.0 | 106.0 | 64.0 | 56.0 | 82.0 |
| | MOISTURE PERCENTAGE | % | 7.4 | 7.1 | 6.7 | 6.7 | 6.8 |
| EVALUATION EQUATION | (EQUATION 1) FREE SENSORY EVALUATION VALUE Ef = −2.879 × (DRY TENSILE STRENGTH IN PAPER HORIZONTAL DIRECTION) + 6.55 × (WET TENSILE STRENGTH IN PAPER HORIZONTAL DIRECTION) + 5.36 | | 4.7 | 4.7 | 3.6 | 3.2 | 4.9 |
| | (EQUATION 2) SLIP SENSORY EVALUATION VALUE Es = −8.80 × (DYNAMIC FRICTION COEFFICIENT) − 0.41 × (ARITHMETIC MEAN SURFACE ROUGHNESS) + 13.58 | | 4.9 | 4.8 | 5.4 | 5.7 | 4.3 |
| SENSORY EVALUATION RESULT | EVALUATION OF "PREFERENCE" | | 4.0 | 4.2 | 4.9 | 5.3 | 3.9 |
| | EVALUATION OF PREFERENCE OF "SOFTNESS" | | 4.0 | 4.6 | 4.3 | 3.6 | 4.9 |
| | EVALUATION OF PREFERENCE OF "SLIPPERINESS" | | 4.0 | 4.2 | 4.8 | 5.3 | 4.2 |

| | | | NON-MOISTURIZING (GENERAL-PURPOSE PRODUCT) COMMERCIAL PRODUCT F | NON-MOISTURIZING (GENERAL-PURPOSE PRODUCT) COMMERCIAL PRODUCT G | NON-MOISTURIZING (GENERAL-PURPOSE PRODUCT) COMMERCIAL PRODUCT H | NON-MOISTURIZING (GENERAL-PURPOSE PRODUCT) COMMERCIAL PRODUCT I | NON-MOISTURIZING (LUXURY PRODUCT) COMMERCIAL PRODUCT j |
|---|---|---|---|---|---|---|---|
| CHEMICAL SOLUTION APPLICATION | CHEMICAL SOLUTION APPLICATION | APPLIED/NOT APPLIED | NOT APPLIED | NOT APPLIED | NOT APPLIED | NOT APPLIED | NOT APPLIED |
| | APPLICATION METHOD | ONE SURFACE/BOTH SURFACES | — | — | — | — | — |

TABLE 1-continued

| | | | | | | | |
|---|---|---|---|---|---|---|---|
| | LOTION CHEMICAL SOLUTION APPLICATION AMOUNT | % BY MASS | 0 | 0 | 0 | 0 | 0 |
| PAPER QUALITY PARAMETER | BASIS WEIGHT (1 SHEET) | g/m² | 12.2 | 10.7 | 11.5 | 10.4 | 14.9 |
| | NUMBER OF PLIES | SHEETS | 2 | 2 | 2 | 2 | 2 |
| | PAPER THICKNESS | μm | 123 | 119 | 107 | 103 | 186 |
| | DRY STRENGTH IN LONGITUDINAL DIRECTION | cN/25 mm | 428.3 | 447.0 | 355.0 | 428.0 | 289.0 |
| | DRY STRENGTH IN HORIZONTAL DIRECTION | cN/25 mm | 80.0 | 133.0 | 140.0 | 134.0 | 119.0 |
| | ELONGATION (LONGITUDINAL DIRECTION) | % | 12.6 | 13.1 | 12.6 | 14.0 | 13.7 |
| | WET STRENGTH IN HORIZONTAL DIRECTION | cN/25 mm | 30.0 | 9.0 | 31.0 | 39.0 | 42.0 |
| | SURFACE ROUGHNESS | μm | 8.5 | 9.2 | 9.0 | 9.5 | 9.4 |
| | AVERAGE FRICTION COEFFICIENT | — | 0.47 | 0.54 | 0.47 | 0.58 | 0.56 |
| | SOFTNESS | cN/100 mm | 0.9 | 1.1 | 1.2 | 1.0 | 1.1 |
| | MMD | — | 6.5 | 9.8 | 7.8 | 7.2 | 7.5 |
| | WEB VOLUME | mm | 62.0 | 41.0 | 47.0 | 47.0 | 73.0 |
| | MOISTURE PERCENTAGE | % | 6.8 | 7.3 | 6.9 | 6.8 | 7.1 |
| EVALUATION EQUATION | (EQUATION 1) FREE SENSORY EVALUATION VALUE Ef = −2.879 × (DRY TENSILE STRENGTH IN PAPER HORIZONTAL DIRECTION) + 6.55 × (WET TENSILE STRENGTH IN PAPER HORIZONTAL DIRECTION) + 5.36 | | 5.0 | 3.4 | 3.4 | 4.1 | 4.7 |
| | (EQUATION 2) SLIP SENSORY EVALUATION VALUE Es = −8.80 × (DYNAMIC FRICTION COEFFICIENT) − 0.41 × (ARITHMETIC MEAN SURFACE ROUGHNESS) + 13.58 | | 5.9 | 5.0 | 5.8 | 4.6 | 4.8 |
| SENSORY EVALUATION RESULT | EVALUATION OF "PREFERENCE" | | 4.3 | 4.8 | 47 | 3.9 | 4.0 |
| | EVALUATION OF PREFERENCE OF "SOFTNESS" | | 4.1 | 3.9 | 3.4 | 3.1 | 4.2 |
| | EVALUATION OF PREFERENCE OF "SLIPPERINESS" | | 4.7 | 4.7 | 4.6 | 3.9 | 4.0 |

From the results of the free sensory evaluation step and the free sensory evaluation analysis step in each sample indicated in Table 1 above, as illustrated in FIG. 4, the following correlation equation (Equation 1) is obtained.

Free sensory evaluation value $E_f = -2.879 \times$ (dry tensile strength in paper horizontal direction) $+ 6.55 \times$ (wet tensile strength in paper horizontal direction) $+ 5.36$   (Equation 1)

In the slip sensory evaluation analysis step, the multiple regression analysis by a stepwise method is performed using the result of the slip sensory evaluation in the slip sensory evaluation step as an objective variable and the paper quality parameter of tissue paper as an explanatory variable. The method of determining the paper quality parameter and the evaluation equation is the same as in the above free sensory evaluation analysis step.

From the results of the slip sensory evaluation step and the slip sensory evaluation analysis step in each sample indicated in Table 1 above, as illustrated in FIG. 5, the following correlation equation (Equation 2) is obtained.

Slip sensory evaluation value $E_s=-8.80\times$(dynamic friction coefficient)$-0.41\times$(arithmetic mean surface roughness)$+13.58$ \hfill (Equation 2)

Here, the measuring methods of the main paper quality parameters of tissue paper are as follows.

Basis Weight

A basis weight is measured based on JIS P 8124 (1998). In the case of multiple plies, measurement is performed for each ply.

Paper Thickness

A test piece is sufficiently moisture-conditioned under the conditions of JIS P 8111 (1998), and then the paper thickness is measured using a dial thickness gauge (thickness measuring instrument) "PEACOCK G type" (made by OZAKI MFG CO., LTD.) under the same conditions. In the case of multiple plies, measurement is performed with multiple plies. In the further specific procedure, a plunger is placed on a measurement stand after confirming that there is no dust or dirt between the plunger and the measuring stand, a memory of the dial thickness gauge is moved to set a zero point, then the plunger is moved up to place a sample on a test stand, the plunger is moved down slowly, and a gauge is read at this time. At this time, the plunger is just placed. A terminal of the plunger is made of metal such that a circular plane with a diameter of 10 mm perpendicularly contacts a paper plane, and the load at the time of measuring the paper thickness is about 70 gf. The thickness is an average value obtained by performing the measurement ten times.

Moisture Content (Moisture Percentage)

After the sample is conditioned under the conditions of JIS P 8111 (1998), the measurement is performed based on JIS P 8127 (1998).

Dry Tensile Strength

Dry tensile strength is measured based on the tensile test of JIS P 8113 (1998).

A test piece used is cut to a width of about 25 mm (±0.5 mm) and a length of about 150 mm in both the longitudinal and horizontal directions. In the case of multi-ply tissue paper, the measurement is performed with multiple plies. As a tester, a load cell tensile tester TG-200N manufactured by Minebea Co., Ltd. is used. A grip interval is set to 100 mm. The measurement is performed in the procedure of tightening both ends of a test piece to grips of the tester, applying a tensile load on the piece of paper in an up-down direction, and reading the indicated value (digital value) when the paper breaks. The pulling speed is 100 mm/min. Five sets of samples are prepared and measured in each of the longitudinal and horizontal directions five times, and the average of the measured values is defined as the dry tensile strength in each direction. (sample preparation is based on JIS P 8111 (1998))

Note that, the unit of the (dry tensile strength in paper horizontal direction) in Equation 1 is N/25 mm.

Wet Tensile Strength

It is measured based on the tensile test of JIS P 8135 (1998).

The test piece used is cut to a width of about 25 mm (±0.5 mm) and a length of about 150 mm in both the vertical and horizontal directions. In the case of multi-ply tissue paper, the measurement is performed with multiple plies. As a tester, a load cell tensile tester TG-200N manufactured by Minebea Co., Ltd. is used. A grip interval is set to 100 mm. The measurement is performed in the procedure of, after tightening both ends of the test piece that has been cured for ten minutes with a dryer at 105° C. to grips of the tester, next applying water horizontally at a width of about 10 mm to the center of the test piece by using a flat brush soaked in water, after that, immediately applying a tensile load to the piece of paper in the up-down direction, and reading the indicated value (digital value) when the paper breaks. The tensile speed is 50 mm/min. Five sets of samples are prepared and measured in each of the longitudinal and horizontal directions five times, and the average of the measured values is defined as the wet tensile strength in each direction.

Note that, the unit of the (wet tensile strength in paper horizontal direction) in Equation 1 is N/25 mm.

Tensile Elongation at Break (Elongation)

Tensile elongation at break is measured based on the tensile test of JIS P 8113 (1998). "Universal tensile and compression tester TG-200N" manufactured by Minebea Co., Ltd. is used.

Softness

The softness is measured based on the handle o-meter method based on JIS L 1096 E method. However, a test piece is made into a size of 100 mm×100 mm, and a clearance is set to 5 mm. The measurement is performed five times each in the longitudinal direction and the lateral direction in one ply, and the average value of all ten times is represented in cN/100 mm.

MMD

While the contact surface of a friction element is brought into contact with the surface of the measurement sample to which a tension of 20 g/cm is applied in a predetermined direction at a contact pressure of 25 g, the friction element is moved by 2 cm at a speed of 0.1 cm/s in substantially the same direction as the direction in which the tension is applied, the friction coefficient at this time is measured using a friction tester KES-SE (manufactured by KATO TECH CO., LTD.). The value obtained by dividing the friction coefficient by a friction distance (moving distance=2 cm) is MMD. The friction element has twenty piano wires P each having a diameter of 0.5 mm adjacent to one another, and has a contact surface formed to have a length and a width of 10 mm. The contact surface is formed with a unit bulging portion whose tip is formed of twenty piano wires P (curvature radius: 0.25 mm).

Dynamic friction coefficient (average friction coefficient μ) Using a tactile force plate TF-2020 (indicated by reference character 5 in the drawing) or its equivalent, sold by Tec Gihan Co., Ltd., a friction coefficient is measured when the same operation as in the slip sensory evaluation test is performed. As illustrated in FIG. 1, tissue paper 3 is placed in a generated state on a plate 6 on a load cell 5A, and one end of tissue paper 3 is fixed on the plate 6 with an adhesive tape 1 or the like. Next, a friction test is performed by sliding a right index finger 2 in one direction perpendicular to the longitudinal direction of the finger so as to trace on the tissue paper 3 to measure a friction coefficient. Note that the tissue paper is fixed such that the sliding direction is the horizontal direction of the paper. In addition, the test is performed such that the vertical load at the time of measurement is about 0.34±0.09N, the sliding speed is 76±23 mm/S, and the sliding distance is 103±15 mm. Note that a measurer may practice several times in advance.

The vertical load and the sliding speed are an average vertical load and an average sliding speed for stably detecting the surface property of tissue paper. The direction of tracing the tissue paper with the right index finger is the direction of the friction felt by the fingertip first. Note that the measurement is performed by nine measures, and the measurement is repeated five times for the same sample (although a notation is changed). The average value excluding an abnormal value is defined as a friction coefficient.

Surface Roughness

The surface roughness is measured according to ISO 25178-2: 2012. In an artificial weather chamber controlled to room temperature 23° C. and relative humidity 50% according to the conditions of JIS P 8111, using a laser microscope VR-3200 manufactured by KEYENCE CORPORATION or its equivalent, the arithmetic average roughness Ra (surface roughness, μm) of test pieces cut into a 10 cm square is calculated according to ISO 25178. In addition, "VR-H1A" manufactured by KEYENCE CORPORATION can be used as software for observing, measuring, and analyzing the image of the laser microscope. Note that, the measurement is performed under the conditions of a magnification of 12 times and a visual field area of 24 mm×18 mm. However, the measurement magnification and the visual field area may be appropriately changed.

The evaluation step evaluates the tissue paper from the free sensory evaluation value calculated according to the regression equation obtained in the free sensory evaluation analysis step and the slip sensory evaluation value calculated according to the regression equation obtained in the slip sensory evaluation analysis step.

The free sensory evaluation value has a correlation with "softness", and the slip sensory evaluation value has a correlation with "slipperiness" as described above. Therefore, each evaluation value is calculated from paper quality parameters, and based on both of the evaluation values, the preference of "softness" and "slipperiness", that is, "smoothness", of tissue paper can be evaluated. In particular, when both "softness" and "smoothness" are excellent, the tissue paper can be evaluated as having excellent usability.

Tissue Paper

First Embodiment

The tissue paper according to the first embodiment according to the present invention is a two-ply non-moisturizing tissue paper to which no chemical solution is applied, a basis weight per sheet is 10.0 to 18.0 g/m², the thickness of two plies is 100 to 240 μm, the free sensory evaluation value $E_f$ calculated according to the following (Equation 1) is 3.7 to 6.6, and the slip sensory evaluation value $E_s$ calculated according to (Equation 2) is 5.0 to 8.2.

Tissue paper is often roughly divided into product groups normally such as, a non-moisturizing type with a basis weight of about 10.0 to 18.0 g/m² to which no chemical solution is applied, and a moisturizing type with a basis weight as high as 14.0 to 22.0 g/m², to which chemical solution is usually applied. The non-moisturizing type with the basis weight of 10.0 to 18.0 g/m² to which no chemical solution is applied can be easily manufactured using the same tissue paper making technology as before.

On the other hand, the tissue paper according to the first embodiment of the present invention has a dry tensile strength of 70 to 180 cN/25 mm in the paper horizontal direction and a wet tensile strength of 25 to 55 cN/25 mm in the paper horizontal direction. Since tissue paper is crepe paper, paper strength is weaker in the horizontal direction of the paper than in the longitudinal direction. When the tensile strength when dry and wet in the horizontal direction is within this range, the tissue paper can be sufficiently used.

$$E_f = -2.879 \times (\text{dry tensile strength in paper horizontal direction}) + 6.55 \times (\text{wet tensile strength in paper horizontal direction}) + 5.36 \quad \text{(Equation 1)}$$

$$E_s = -8.80 \times (\text{dynamic friction coefficient}) - 0.41 \times (\text{arithmetic mean surface roughness}) + 13.58 \quad \text{(Equation 2)}$$

Figure 6:
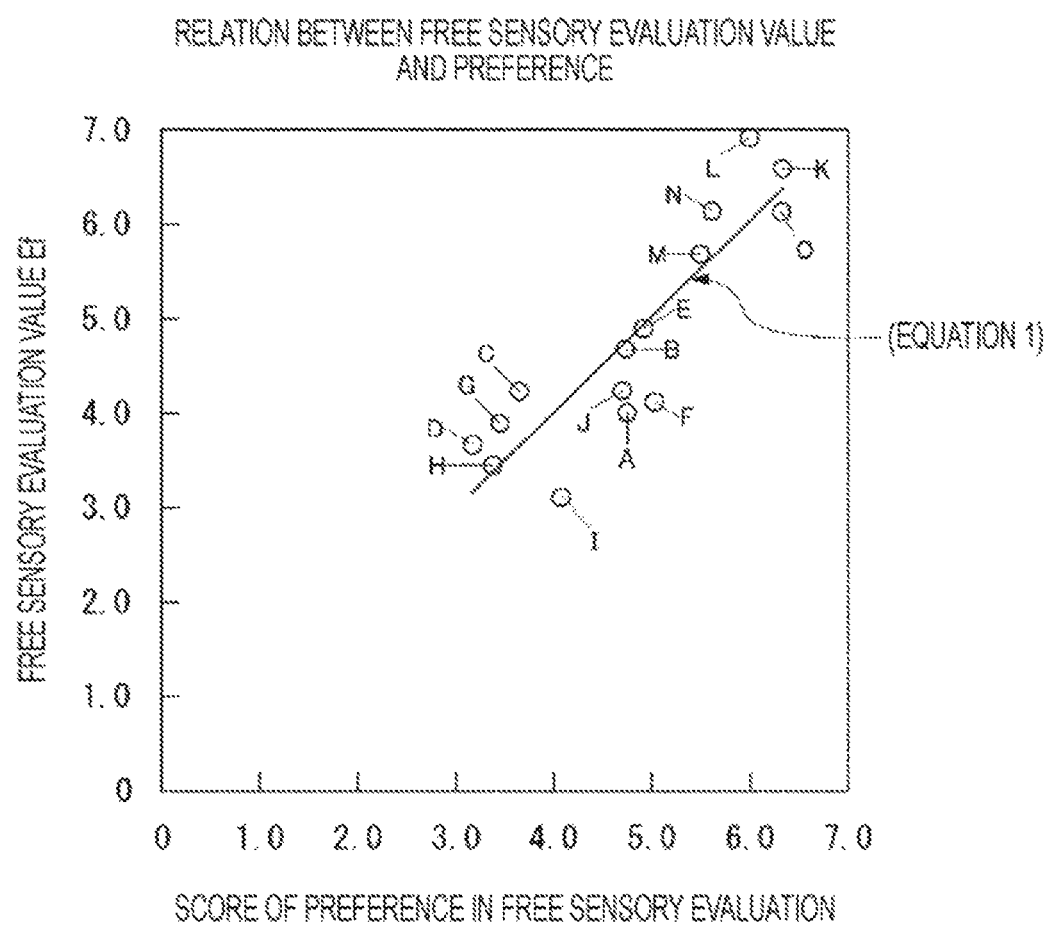
FIG. 6 is a graph for explaining a correlation equation (Equation 1) according to the present invention.

When the range of (Equation 1) and (Equation 2) is within the above range, as indicated in Table 1 and FIGS. 6 and 7, non-moisturizing tissue paper with unprecedented excellent "softness" and "smoothness" is obtained.

These correlation expressions are obtained as the results of the free sensory evaluation step/free sensory evaluation analysis step and the slip sensory evaluation step/slip sensory evaluation analysis step for each sample of the conventional product shown in Table 1 above, based on the method of evaluating tissue paper according to the present invention. Note that these sensory evaluations are performed by nine evaluators, each sample is evaluated five times per evaluator, and the average of the scores excluding an abnormal value score is defined as the evaluator's score in a certain sample. Further, scoring is performed by scoring one to seven points for each sample with the score of most commonly used sample A on the market set to four points, and calculating the average value of each evaluator. The sensory evaluation is performed by nine evaluators, and if each evaluator performs five evaluations on each sample, a sufficiently unbiased evaluation is possible. Further, tissue paper generally has product category of moisturizing tissue paper, luxury non-moisturizing tissue paper products, and general-purpose non-moisturizing tissue paper products. If total fifteen types of samples, including five types of moisturizing tissue paper, three types of luxury non-moisturizing tissue paper products, and seven types of non-moisturizing tissue paper general-purpose products, are taken, existing tissue paper can be generally evaluated, and a correlation equation can be obtained. Sample A which is a reference sample is non-moisturizing tissue paper with the highest market share and is a sample most consumers touch.

Since the free sensory evaluation value $E_f$ in (Equation 1) is determined by the dry tensile strength and the wet tensile strength in the horizontal direction, in particular, to make the free sensory evaluation value $E_f$ in the range of 3.7 to 6.6, it can be adjusted by paper strength agents of a dry paper strength agent and a wet paper strength agent, and discharging of a papermaking raw material at the time of pulp blending and papermaking. In particular, the paper strength in the horizontal direction is less dependent on crepes, such that the adjustment with the paper strength agents is effective. Here, examples of the dry paper strength agent include cationic starch and cationic or amphoteric polyacrylamide copolymers, and examples of the wet paper strength agent include urea formaldehyde resin, melamine formaldehyde resin, polyamide polyamine epichlorohydrin (PAE), and polyvinyl amines (PVAm). Further, a raw material pulp is a mixture of softwood kraft pulp abbreviated as NBKP and hardwood kraft pulp abbreviated as LBKP. The blending ratio is selected from NBKP:LBKP=20:80 to 80:20, and is particularly desirably NBKP:LBKP=50:50 to 45:55. If the blending ratio of NBKP is slightly larger than the blending ratio of pulp in general non-moisturizing tissue paper, paper strength can be easily adjusted to the range of the present invention.

The slip sensory evaluation value $E_s$ calculated according to (Equation 2) is determined by the dynamic friction coefficient and the arithmetic mean roughness. In particular, to make the slip sensory evaluation value $E_s$ in the range of 5.0 to 8.2, it can be adjusted by adjusting a crepe ratio, the adjustment of a creping doctor, the mixing ratio of pulp, and an internal softener for coating a pulp fiber.

Second Embodiment

On the other hand, the tissue paper according to a second embodiment of the present invention is a two-ply moisturizing tissue paper to which a chemical solution is applied, and has a basis weight per sheet of 14.0 to 22.0 g/m², the thickness of 120 to 250 μm, the free sensory evaluation value $E_f$ calculated according to the above (Equation 1) is 6.0 to 8.4, and the slip sensory evaluation value $E_s$ calculated according to the above (Equation 2) is 5.3 to 8.0.

The non-moisturizing type with a basis weight of 14.0 to 22.0 g/m² to which a chemical solution is applied can be easily manufactured using the conventional tissue paper making technology.

On the other hand, the tissue paper according to the second embodiment of the present invention has a dry tensile strength of 50 to 120 cN/25 mm in the paper horizontal direction and a wet tensile strength of 30 to 90 cN/25 mm in the paper horizontal direction. Since tissue paper is crepe paper, paper strength is weaker in the horizontal direction of the paper than in the longitudinal direction. If the tensile strength when dry and wet in the horizontal direction is within this range, the tissue paper can be sufficiently used.

When the range of (Equation 1) and (Equation 2) is within the above range, moisturizing tissue paper with unprecedented excellent "softness" and "smoothness" is obtained.

These correlation expressions are obtained in the same manner as the tissue paper according to the first embodiment. Here, since the free sensory evaluation value $E_f$ in (Equation 1) is determined by the dry tensile strength and the wet tensile strength in the horizontal direction, in particular, to make the free sensory evaluation value $E_f$ in the range of 6.0 to 8.4, it can be adjusted by paper strength agents of a dry paper strength agent and a wet paper strength agent, and discharging of a papermaking raw material at the time of pulp blending and papermaking. In particular, the paper strength in the horizontal direction is less dependent on crepes, such that the adjustment with the paper strength agents is effective. Specific examples of the dry strength agent and the wet paper strength agent and the raw pulp are the same as in the first embodiment. Further, in the case of moisturizing tissue paper, it is particularly desirable to reduce the difference between the dry tensile strength in the paper horizontal direction of the paper and the wet tensile strength in the paper horizontal direction. Specifically, the difference between the dry tensile strength in the paper horizontal direction and the wet tensile strength in the paper horizontal direction is desirably 19 to 44 cN/25 mm. Further, the dry tensile strength and the wet tensile strength of a base paper are preferably increased such that the amount of a moisturizing agent tends to be as large as 20.0 to 30.0%.

The slip sensory evaluation value $E_s$ calculated according to (Equation 2) is determined by the dynamic friction coefficient and the arithmetic mean roughness. In particular, to make the slip sensory evaluation value $E_s$ in the range of 5.0 to 8.2, it can be adjusted by adjusting a crepe ratio, the adjustment of a creping doctor, the mixing ratio of pulp, and an internal softener for coating a pulp fiber as with the first embodiment.

EXAMPLES

Then, based on the above Equations 1 and 2, the manufactured moisturizing tissue paper (Example 1) and the non-moisturizing tissue paper (Example 2) according to the present invention were subjected to free sensory evaluation and slip sensory evaluation. Table 2 below indicates the physical property values and evaluation values of Example 1 and Example 2. Note that Table 2 also indicates the physical property values and evaluation values of each sample according to the conventional example indicated in Table 1.

Here, Example 1 is a two-ply moisturizing tissue paper to which a chemical solution is applied. In Example 1, the raw material pulp was blended such that the ratio of NBKP:LBKP is 50:50, and the ratio of NBKP was slightly higher, and was subjected to paper making with a circular net Yankee dryer paper machine. To adjust a friction coefficient, a doctor blade angle and a crepe ratio were adjusted.

A total of 25.5% of chemical solution was applied by flexographic printing to both surfaces of laminated tissue paper base paper in which two sheets of tissue paper base paper were laminated.

The chemical solution used is an aqueous chemical solution containing glycerin as a main component, and contains 85% by mass of glycerin, 10% by mass of water, and 5% by mass of functional agents such as a softener and liquid paraffin. The viscosity of the aqueous chemical solution was 110 mPa-s at 40° C.

The laminated continuous sheet to which the chemical solution was applied was processed by a rotary inter folder to obtain a cut sheet. Note that the tension was adjusted in the rotary inter folder.

In the tissue paper product created, a basis weight per ply was 17.6 g/m², the paper thickness of two plies was 138 μm, the dry tensile strength in the paper horizontal direction was 131 cN/25 mm, and the wet tensile strength in the paper horizontal direction was 85 cN/25 mm. Note that the paper strength was adjusted by adjusting the content of a known paper strength agent. The content was about 12.0 kg/pulpton by internal addition.

In Example 1, the free sensory evaluation value $E_f$ calculated according to Equation 1 is 7.2, and the slip sensory evaluation value $E_s$ calculated according to Equation 2 is 6.3.

Example 2 is a two-ply tissue paper to which no chemical is applied. In Example 2, NBKP:LBKP ratio was set to 50:50 and the papermaking was performed with a circular net Yankee dryer paper machine. A laminated continuous sheet obtained by laminating two sheets of tissue paper base paper to form a laminated tissue paper base paper was processed by a rotary inter-folder to obtain a cut sheet.

In the tissue paper product created, a basis weight per ply was 14.9 g/m², the paper thickness of two plies was 181 μm, the dry tensile strength in the paper horizontal direction was 109 cN/25 mm, and the wet tensile strength in the paper horizontal direction was 60.7 cN/25 mm.

The free sensory evaluation value $E_f$ calculated according to Equation 2 in Example 1 is 6.2, and the slip sensory evaluation value $E_s$ calculated according to Equation 2 is 6.1. The adjustment of the paper strength and the friction coefficient were performed in the same manner as in Example 1.

TABLE 2

| | | | MOISTURIZING EXAMPLE 1 | MOISTURIZING COMMERCIAL PRODUCT K | MOISTURIZING COMMERCIAL PRODUCT L | MOISTURIZING COMMERCIAL PRODUCT M | MOISTURIZING COMMERCIAL PRODUCT N | MOISTURIZING COMMERCIAL PRODUCT O |
|---|---|---|---|---|---|---|---|---|
| CHEMICAL SOLUTION APPLICATION | CHEMICAL SOLUTION APPLICATION | APPLIED/NOT APPLIED | APPLIED | APPLIED | APPLIED | APPLIED | APPLIED | APPLIED |
| | APPLICATION METHOD | ONE SURFACE/BOTH SURFACES | BOTH SURFACES | BOTH SURFACES | BOTH SURFACES | ONE SURFACE | BOTH SURFACES | BOTH SURFACES |
| | LOTION CHEMICAL SOLUTION APPLICATION AMOUNT | % BY MASS | 25.5 | 25.5 | 24.3 | 15.0 | 20.0 | 19.5 |
| PAPER QUALITY PARAMETER | BASIS WEIGHT (1 SHEET) | g/m$^2$ | 17.6 | 17.5 | 18.0 | 14.7 | 16.2 | 14.3 |
| | NUMBER OF PLIES | SHEETS | 2 | 2 | 2 | 2 | 2 | 2 |
| | PAPER THICKNESS | μm | 138 | 151 | 174 | 140 | 156 | 139 |
| | DRY STRENGTH IN LONGITUDINAL DIRECTION | cN/25 mm | 342.0 | 194.0 | 238.0 | 253.0 | 330.0 | 216.0 |
| | DRY STRENGTH IN HORIZONTAL DIRECTION | cN/25 mm | 131.0 | 80.0 | 51.0 | 73.0 | 85.0 | 83.0 |
| | ELONGATION (LONGITUDINAL DIRECTION) | % | 14.5 | 12.4 | 14.5 | 13.1 | 11.3 | 14.6 |
| | WET STRENGTH IN HORIZONTAL DIRECTION | cN/25 mm | 85.0 | 50.0 | 32.0 | 34.0 | 41.0 | 51.0 |
| | SURFACE ROUGHNESS | μm | 9.0 | 10.0 | 8.5 | 9.7 | 8.6 | 9.7 |
| | AVERAGE FRICTION COEFFICIENT | — | 0.41 | 0.48 | 0.47 | 0.52 | 0.54 | 0.50 |
| | SOFTNESS | cN/100 mm | 1.2 | 0.9 | 1.0 | 0.7 | 0.8 | 0.9 |
| | MMD | — | 6.9 | 8.2 | 5.6 | 7.7 | 6.4 | 7.4 |
| | WEB VOLUME | mm | 70.3 | 80.0 | 83.0 | 58.0 | 82.0 | 60.0 |
| | MOISTURE PERCENTAGE | % | 14.5 | 12.6 | 8.6 | 9.0 | 9.3 | 10.3 |
| EVALUATION EQUATION | (EQUATION 1) FREE SENSORY EVALUATION VALUE Ef = −2.879 × (DRY TENSILE STRENGTH IN PAPER HORIZONTAL DIRECTION) + 6.55 × (WET TENSILE STRENGTH IN PAPER HORIZONTAL DIRECTION) + 5.36 | | 7.2 | 6.3 | 6.0 | 5.5 | 5.6 | 6.3 |
| | (EQUATION 2) SLIP SENSORY EVALUATION VALUE Es = −8.80 × (DYNAMIC FRICTION COEFFICIENT) − 0.41 × (ARITHMETIC MEAN SURFACE ROUGHNESS) + 13.58 | | 6.3 | 5.3 | 6.0 | 5.0 | 5.3 | 5.2 |

TABLE 2-continued

| | | | | | | | | |
|---|---|---|---|---|---|---|---|---|
| SENSORY EVALUATION RESULT SEVEN POINT EVALUATION | EVALUATION OF PREFERENCE OF "SOFTNESS" | | 7.4 | 6.5 | 6.9 | 5.7 | 6.1 | 6.1 |
| | EVALUATION OF PREFERENCE OF "SLIPPERINESS" | | 6.5 | 5.9 | 6.0 | 4.0 | 5.6 | 4.2 |

| | | | NON-MOISTURIZING EXAMPLE 2 | NON-MOISTURIZING COMMERCIAL PRODUCT A | NON-MOISTURIZING COMMERCIAL PRODUCT B | NON-MOISTURIZING COMMERCIAL PRODUCT C | NON-MOISTURIZING COMMERCIAL PRODUCT D | NON-MOISTURIZING COMMERCIAL PRODUCT E |
|---|---|---|---|---|---|---|---|---|
| CHEMICAL SOLUTION APPLICATION | CHEMICAL SOLUTION APPLICATION | APPLIED/NOT APPLIED | NOT APPLIED | NOT APPLIED | NOT APPLIED | NOT APPLIED | NOT APPLIED | NOT APPLIED |
| | APPLICATION METHOD | ONE SURFACE/BOTH SURFACES | — | — | — | — | — | — |
| | LOTION CHEMICAL SOLUTION APPLICATION AMOUNT | % BY MASS | 0 | 0 | 0 | 0 | 0 | 0 |
| PAPER QUALITY PARAMETER | BASIS WEIGHT (1 SHEET) | g/m$^2$ | 14.9 | 13.3 | 16.1 | 13.3 | 11.0 | 14.6 |
| | NUMBER OF PLIES | SHEETS | 2 | 2 | 2 | 2 | 2 | 2 |
| | PAPER THICKNESS | μm | 181 | 142 | 190 | 123 | 101 | 205 |
| | DRY STRENGTH IN LONGITUDINAL DIRECTION | cN/25 mm | 289.0 | 394.0 | 289.3 | 259.0 | 524.0 | 320.5 |
| | DRY STRENGTH IN HORIZONTAL DIRECTION | cN/25 mm | 109.0 | 90.0 | 102.0 | 142.0 | 161.0 | 84.0 |
| | ELONGATION (LONGITUDINAL DIRECTION) | % | 19.2 | 14.3 | 14.2 | 13.5 | 14.8 | 14.1 |
| | WET STRENGTH IN HORIZONTAL DIRECTION | cN/25 mm | 60.7 | 30.0 | 35.0 | 36.0 | 37.0 | 30.0 |
| | SURFACE ROUGHNESS | μm | 8.7 | 10.5 | 8.6 | 10.0 | 8.1 | 10.4 |
| | AVERAGE FRICTION COEFFICIENT | — | 0.45 | 0.50 | 0.60 | 0.47 | 0.52 | 0.57 |
| | SOFTNESS | cN/100 mm | 1.0 | 1.1 | 1.1 | 1.2 | 1.0 | 0.9 |
| | MMD | — | 6.6 | 7.0 | 5.7 | 7.8 | 7.0 | 7.4 |
| | WEB VOLUME | mm | 73.0 | 62.0 | 106.0 | 64.0 | 56.0 | 82.0 |
| | MOISTURE PERCENTAGE | % | 7.1 | 7.4 | 7.1 | 6.7 | 6.7 | 6.8 |
| EVALUATION EQUATION | (EQUATION 1) FREE SENSORY EVALUATION VALUE Ef = −2.879 × (DRY TENSILE STRENGTH IN PAPER HORIZONTAL DIRECTION) + 6.55 × (WET TENSILE STRENGTH IN PAPER HORIZONTAL DIRECTION) + 5.36 | | 6.2 | 4.7 | 4.7 | 3.6 | 3.2 | 4.9 |

TABLE 2-continued

| | | | | | | | |
|---|---|---|---|---|---|---|---|
| | (EQUATION 2) SLIP SENSORY EVALUATION VALUE Es = −8.80 × (DYNAMIC FRICTION COEFFICIENT) − 0.41 × (ARITHMETIC MEAN SURFACE ROUGHNESS) + 13.58 | | 6.1 | 4.9 | 4.8 | 5.4 | 5.7 | 4.3 |
| SENSORY EVALUATION RESULT SEVEN POINT EVALUATION | EVALUATION OF PREFERENCE OF "SOFTNESS" | | 6.5 | 4.0 | 4.6 | 4.3 | 3.6 | 4.9 |
| | EVALUATION OF PREFERENCE OF "SLIPPERINESS" | | 5.5 | 4.0 | 4.2 | 4.8 | 5.3 | 4.2 |

| | | | NON-MOISTURIZING COMMERCIAL PRODUCT F | NON-MOISTURIZING COMMERCIAL PRODUCT G | NON-MOISTURIZING COMMERCIAL PRODUCT H | NON-MOISTURIZING COMMERCIAL PRODUCT I | NON-MOISTURIZING COMMERCIAL PRODUCT J |
|---|---|---|---|---|---|---|---|
| CHEMICAL SOLUTION APPLICATION | CHEMICAL SOLUTION APPLICATION | APPLIED/ NOT APPLIED | NOT APPLIED | NOT APPLIED | NOT APPLIED | NOT APPLIED | NOT APPLIED |
| | APPLICATION METHOD | ONE SURFACE/ BOTH SURFACES | — | — | — | — | — |
| | LOTION CHEMICAL SOLUTION APPLICATION AMOUNT | % BY MASS | 0 | 0 | 0 | 0 | 0 |
| PAPER QUALITY PARAMETER | BASIS WEIGHT (1 SHEET) | g/m$^2$ | 12.2 | 10.7 | 11.5 | 10.4 | 14.9 |
| | NUMBER OF PLIES | SHEETS | 2 | 2 | 2 | 2 | 2 |
| | PAPER THICKNESS | μm | 123 | 98 | 107 | 110 | 165 |
| | DRY STRENGTH IN LONGITUDINAL DIRECTION | cN/25 mm | 428.3 | 447.0 | 355.0 | 428.0 | 289.0 |
| | DRY STRENGTH IN HORIZONTAL DIRECTION | cN/25 mm | 80.0 | 133.0 | 140.0 | 134.0 | 119.0 |
| | ELONGATION (LONGITUDINAL DIRECTION) | % | 12.6 | 13.1 | 12.6 | 14.0 | 13.7 |
| | WET STRENGTH IN HORIZONTAL DIRECTION | cN/25 mm | 30.0 | 29.0 | 31.0 | 39.0 | 42.0 |
| | SURFACE ROUGHNESS | μm | 8.5 | 9.2 | 9.0 | 9.5 | 9.4 |
| | AVERAGE FRICTION COEFFICIENT | — | 0.48 | 0.54 | 0.47 | 0.58 | 0.56 |
| | SOFTNESS | cN/100 mm | 0.9 | 1.1 | 1.2 | 1.0 | 1.1 |
| | MMD | — | 6.5 | 9.8 | 7.8 | 7.2 | 7.5 |
| | WEB VOLUME | mm | 62.0 | 41.0 | 47.0 | 47.0 | 73.0 |
| | MOISTURE PERCENTAGE | % | 6.8 | 7.3 | 6.9 | 6.8 | 7.1 |

TABLE 2-continued

| EVALUATION EQUATION | (EQUATION 1) FREE SENSORY EVALUATION VALUE Ef = −2.879 × (DRY TENSILE STRENGTH IN PAPER HORIZONTAL DIRECTION) + 6.55 × (WET TENSILE STRENGTH IN PAPER HORIZONTAL DIRECTION) + 5.36 | 5.0 | 3.4 | 3.4 | 4.1 | 4.7 |
|---|---|---|---|---|---|---|
| | (EQUATION 2) SLIP SENSORY EVALUATION VALUE Es = −8.80 × (DYNAMIC FRICTION COEFFICIENT) − 0.41 × (ARITHMETIC MEAN SURFACE ROUGHNESS) + 13.58 | 5.9 | 5.0 | 5.8 | 4.6 | 4.8 |
| SENSORY EVALUATION RESULT | EVALUATION OF PREFERENCE OF "SOFTNESS" | 4.1 | 3.9 | 3.4 | 3.1 | 4.2 |
| SEVEN POINT EVALUATION | EVALUATION OF PREFERENCE OF "SLIPPERINESS" | 4.7 | 4.7 | 4.6 | 3.9 | 4.0 |

The values of the free sensory evaluation and the slip sensory evaluation in Example 1 and Example 2 are significantly better than those of the conventional samples. That is, it can be said that the tissue paper according to the present invention is soft and smooth tissue paper not found in conventional products.

REFERENCE SIGNS LIST 1 adhesive tape
2 index finger
3 tissue paper
5 tactile force plate
5A load cell
6 plate

The invention claimed is:

1. Tissue paper that is two-ply non-moisturizing tissue paper to which no chemical solution is applied,
wherein a basis weight per sheet is 10.0 to 18.0 g/m$^2$, a thickness of two plies is 100 to 240 μm,
a dry tensile strength in a paper horizontal direction is 70 to 180 cN/25 mm,
a wet tensile strength in a paper horizontal direction is 25 to 55 cN/25 mm,
a free sensory evaluation value $E_f$ is 3.7 to 6.6, where $E_f = -2.879 \times$(dry tensile strength in paper horizontal direction in N/25 mm)$+6.55 \times$(wet tensile strength in paper horizontal direction in N/25 mm)$+5.36$, and
a slip sensory evaluation value $E_S$ is 5.0 to 8.2, where $E_s = -8.80 \times$(dynamic friction coefficient)$-0.41 \times$(arithmetic mean surface roughness)$+13.58$.

* * * * *